United States Patent [19]
Gehring et al.

[11] Patent Number: 4,771,066
[45] Date of Patent: Sep. 13, 1988

[54] 4-HALOALKYLTHIO-5-AMINO-1-ARYL-PYRAZOLES, COMPOSITION CONTAINING THEM, AND INSECTICIDAL AND ACARICIDAL METHOD OF USING THEM

[75] Inventors: Reinhold Gehring, Wuppertal; Uta Jensen-Korte, Duesseldorf; Otto Schallner, Monheim; Jörg Stetter, Wuppertal; Heinz-Jürgen Wroblowsky, Langenfeld; Benedikt Becker, Mettmann; Wolfgang Behrenz, Overath; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 13,741

[22] Filed: Feb. 12, 1987

[30] Foreign Application Priority Data

Feb. 28, 1986 [DE] Fed. Rep. of Germany ....... 3606476

[51] Int. Cl.$^4$ ................... A01N 43/56; C07D 231/44
[52] U.S. Cl. .................... 514/404; 514/212; 514/232; 514/326; 514/407; 514/236.5; 540/603; 544/140; 546/211; 546/279; 548/362; 548/374; 548/376
[58] Field of Search ....... 548/362, 374, 376; 546/279, 211; 514/341, 404, 407, 212, 232, 326; 544/140; 540/603

[56] References Cited

U.S. PATENT DOCUMENTS

4,127,575 11/1978 McGreoger ............ 546/345

FOREIGN PATENT DOCUMENTS

2839270 3/1980 Fed. Rep. of Germany ...... 548/375
3402308 8/1985 Fed. Rep. of Germany ...... 548/362

OTHER PUBLICATIONS

Giori et al., Farmaco Ed. Sci., 38, pp. 274–284, (1983).
Ahmad et al., J. Org. Chem., 36, pp. 2972–2974, (1971).
Coburn, J. Heterocycles Chemistry, 7, pp. 345–349, (1970).
Takamizawa et al., C.A., 62, 13137c, (1965).
Gais et al., Heterocyclices, 4, pp. 192–1932, (1976).
Elguero et al., Bull. Soc. Chim., France, (1970), pp. 4436–4438.
Fusco et al., Gazz. Chim., Ital., 97, pp. 410–420, (1967).
Elguero et al., Bull. Soc. Chim., France, 1966, pp. 3744–3752.
Zauhar et al., Canad. J. Chem., 46, pp. 1079–1091, (1968).
Elguero et al., Bull. Soc. Chim., France, 1968, pp. 5019–5029.
Ohse et al., Tetrahedron Letters, 1968, pp. 1949–1951.
Khan et al., J. Heterocycl. Chem., 18, pp. 9–14, (1981).
Giori et al., Farmaco. Ed. Sci., 26, pp. 276–293, (1971).
Vannini et al., MycopathoLogics, 74, pp. 7–14, (1981).
Collins et al., J. Chem. Soc. C, 1971, pp. 167–174.
Leibscher et al., C.A., 101, 230514d—p. 771.

*Primary Examiner*—Richard A. Schwartz
*Assistant Examiner*—Kurt G. Briscoe
*Attorney, Agent, or Firm*—Sprung Horn Kramer & Woods

[57] ABSTRACT

Insecticidally and acarididally active 1-arylpyrazoles of the formula

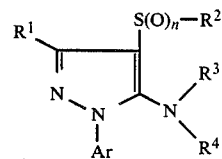

in which
  $R^1$ represents hydrogen, alkyl or halogen alkyl,
  $R^2$ represents alkyl, alkenyl, alkinyl, cycloalkyl, halogenoalkyl, halogenoalkenyl, alkoxyalkyl, alkylthioalkyl, alkylsulphinylalkyl, alkylsulphonylalkyl, optionally substituted aralkyl or optionally substituted aryl,
  $R^3$ represents alkyl, alkenyl, alkinyl, halogenoalkyl, halogenoalkenyl, alkoxyalkyl, alkylthioalkyl, cycloalkyl or optionally substituted aralkyl,
  $R^4$ represents alkyl, alkenyl, alkinyl, halogenoalkyl, halogenoalkenyl, alkoxyalkyl, alkylthioalkyl, cycloalkyl or optionally substituted aralkyl, and, in addition, also represents hydrogen in the case where $R^3$ does not simultaneously represent unsubstituted alkyl, or
  $R^3$ and $R^4$, together with the nitrogen atom to which they are bound, represent a saturated heterocycle, which can optionally contain further heteroatoms,
  Ar represents in each case optionally substituted phenyl or pyridyl, and
  n represents a number 0, 1 or 2.

12 Claims, No Drawings

4-HALOALKYLTHIO-5-AMINO-1-ARYL-PYRAZOLES, COMPOSITION CONTAINING THEM, AND INSECTICIDAL AND ACARICIDAL METHOD OF USING THEM

The invention relates to new 1-arylpyrazoles, a process for their preparation, and their use as pesticides, particularly as insecticides and acaricides.

It is already known that certain pyrazole derivatives, such as, for example, 1-cyclohexyl-5-[N,N-(dimethyl)-carbamoyloxy]-3-methylthiomethyl-pyrazole, 1-cyclohexyl-5-[N,N-(dimethyl)-carbamoyloxy]-3-methylsulphinyl-methyl-pyrazole or 1-cyclohexyl-5-[N,N-(dimethyl)-carbamoyloxy]-3-methylsulphonyl-methyl-pyrazole have an insecticidal action (cf. DE-OS (German Published Specification) No. 2,839,270).

However, the strength of action or duration of action of these compounds is not always completely satisfactory in all areas of application, particularly for certain insects or at low concentrations.

New 1-aryl-pyrazoles of the general formula (I)

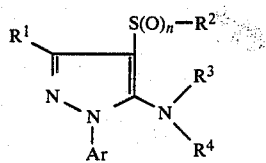   (I)

in which
R$^1$ represents hydrogen, alkyl or halogenoalkyl,
R$^2$ represents alkyl, alkenyl, alkinyl, cycloalkyl, halogenoalkyl, halogenoalkenyl, alkoxyalkyl, alkylthioalkyl, alkylsulphinylalkyl, alkylsulphonylalkyl, optionally substituted aralkyl or optionally substituted aryl,
R$^3$ represents alkyl, alkenyl, alkinyl, halogenoalkyl, halogenoalkenyl, alkoxyalkyl, alkylthioalkyl, cycloalkyl or optionally substituted aralkyl,
R$^4$ represents alkyl, alkenyl, alkinyl, halogenoalkyl, halogenoalkenyl, alkoxyalkyl, alkylthioalkyl, cycloalkyl or optionally substituted aralkyl, and, in addition, also represents hydrogen in the case where R$^3$ does not simultaneously represent unsubstituted alkyl, or
R$^3$ and R$^4$, together with the nitrogen atom to which they are bound, represents a saturated heterocycle, which can optionally contain further heteroatoms,
Ar represents in each case optionally substituted phenyl or pyridyl, and
n represents a number 0, 1 or 2,
have now been found.

It has furthermore been found that the new 1-aryl-pyrazoles of the general formula (I)

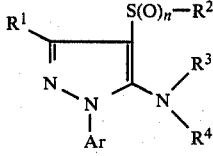   (I)

in which
R$^1$ represents hydrogen, alkyl or halogenoalkyl,
R$^2$ represents alkyl, alkenyl, alkinyl, cycloalkyl, halogenoalkyl, halogenoalkenyl, alkoxyalkyl, alkylthioalkyl, alkylsulphinylalkyl, alkylsulphonylalkyl, optionally substituted aralkyl or optionally substituted aryl,
R$^3$ represents alkyl, alkenyl, alkinyl, halogenoalkyl, halogenoalkenyl, alkoxyalkyl, alkylthioalkyl, cycloalkyl or optionally substituted aralkyl,
R$^4$ represents alkyl, alkenyl, alkinyl, halogenolkyl, halogenoalkenyl, alkoxyalkyl, alkylthioalkyl, cycloalkyl or optionally substituted aralkyl and, additionally, also represents hydrogen in the case where R$^3$ does not simultaneously represent unsubstituted alkyl, or
R$^3$ and R$^4$, together with the nitrogen atom to which they are bound, represent a saturated heterocycle, which can optionally contain further heteroatoms,
Ar represents in each case optionally substituted phenyl or pyridyl, and
n represents a number 0, 1 or 2,
are obtained with the aid of the process described below:

1-Aryl-pyrazoles of the formula (I) are obtained when
(a) 5-halogeno-1-aryl-pyrazoles of the formula (II),

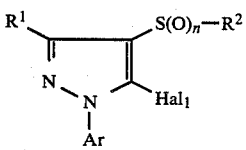   (II)

in which
R$^1$, R$^2$, n and Ar have the abovementioned meaning and
Hal$^1$ represents halogen,
are reacted with amines of the formula (III),

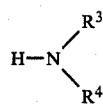   (III)

in which R$^3$ and R$^4$ have the abovementioned meaning, if appropriate in the presence of a diluent and if appropriate in the presence of an acid acceptor,
(b) 5-amino-1-aryl-pyrazoles of the formula

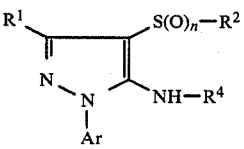   (IV)

in which R$^1$, R$^2$, R$^4$, n and Ar have the abovementioned meaning, are reacted with alkylating agents of the formula (V)

R$^3$-E$^1$   (V)

in which
R$^3$ has the abovementioned meaning and
E$^1$ represents an electron-withdrawing leaving group,
if appropriate in the presence of a diluent, if appropriate in the presence of an acid acceptor and if appropriate in the presence of a catalyst;

1-aryl-pyrazoles of the formula (Ia),

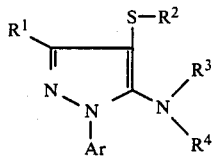   (Ia)

in which $R^1$, $R^2$, $R^3$, $R^4$ and Ar have the abovementioned meaning, are alternatively obtained when (c) 4-unsubstituted 1-aryl-pyrazoles of the formula (VI),

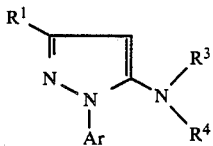   (VI)

in which $R^1$, $R^3$, $R^4$ and Ar have the abovementioned meaning, are reacted with sulphenyl halides of the formula (VII),

 $R^2$-S-Hal$^2$   (VII)

in which
$R^2$ has the abovementioned meaning and
Hal$^2$ represents halogen,
if appropriate in the presence of a diluent and if appropriate in the presence of an acid acceptor;
1-aryl-pyrazoles of the formula (Ib),

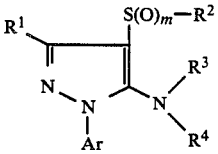   (Ib)

in which
$R^1$, $R^2$, $R^3$, $R^4$ and Ar have the abovementioned meaning and
m represents a number 1 or 2,
are alternatively obtained when (d) the 1-aryl-pyrazoles of the formula (Ia),

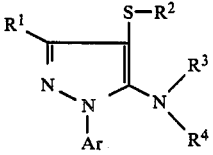   (Ia)

in which $R^1$, $R^2$, $R^3$, $R^4$ and Ar have the abovementioned meaning, which are obtained by process (a), (b) or (c) are oxidized on the sulphur of the sulphenyl group in the 4-position of the pyrazole ring using oxidants of the formula (VIII),

 $R^5$-O-O-H   (VIII)

in which $R^5$ represents hydrogen or in each case optionally substituted alkanoyl or aroyl, if appropriate in the presence of a diluent, if appropriate in the presence of a catalyst and if appropriate in the presence of an acid acceptor.

Finally, it has been found that the new 1-aryl-pyrazoles of the general formula (I) have strongly developed insecticidal and acaricidal properties.

Surprisingly, the 1-aryl-pyrazoles, according to the invention, of the general formula (I) display a considerably better insecticidal and acaricidal activity than the pyrazole derivatives which are known from the state of the art, such as, for example, 1-cyclohexyl-5-[N,N-(dimethyl)-carbamoyloxy]-3-methylthiomethyl-pyrazole, 1-cyclohexyl-5-[N,N-(dimethyl)-carbamoyloxy]-3-methylsulphinylpyrazole or 1-cyclohexyl-5-[N,N-(dimethyl)-carbamoyloxy]-3-methylsulphonylmethyl-pyrazole, which are similar compounds chemically and with respect to their action.

The 1-aryl-pyrazoles according to the invention are generally defined by the formula (I). Preferred compounds of the formula (I) are those in which $R^1$ represents hydrogen, or in each case straight-chain or branched alkyl or halogenoalkyl having 1 to 4 carbon atoms and, if appropriate, 1 to 9 identical or different halogen atoms, $R^2$ represents in each case straight-chain or branched alkyl, alkenyl or alkinyl having up to 8 carbon atoms in each case, cycloalkyl having 3 to 7 carbon atoms, in each case straight-chain or branched halogenoalkyl or halogenoalkenyl having up to 8 carbon atoms in each case and up to 17 identical or different halogen atoms, in each case straight-chain or branched alkoxyalkyl, alkylthioalkyl, alkylsulphinylalkyl or alkylsulphonylalkyl having, in each case, 1 to 6 carbon atoms in the individual alkyl parts, or in each case optionally mono- or polysubstituted phenylalkyl or phenyl having, if appropriate, 1 to 4 carbon atoms in the straight-chain or branched alkyl part, the substituents in each case being in the phenyl part and being identical or different and suitable substituents in the phenyl part in each case being: halogen, cyano, nitro, in each case straight-chain or branched alkyl, alkoxy, alkylthio, alkylsulphinyl, alkylsulphonyl, halogenoalkyl, halogenoalkoxy, halogenoalkylthio, halogenoalkylsulphinyl or halogenoalkylsulphonyl in each case having 1 to 4 carbon atoms in the individual alkyl part and, if appropriate, 1 to 9 identical or different halogen atoms, $R^3$ represents in each case straight-chain or branched alkyl, alkenyl, alkinyl, halogenoalkyl or halogenoalkenyl, in each case having up to 8 carbon atoms and, if appropriate, having 1 to 17 halogen atoms, additionally represents in each case straight-chain or branched alkoxyalkyl or alkylthioalkyl in each case having 1 to 4 carbon atoms in the individual alkyl parts, cycloalkyl having 3 to 7 carbon atoms or optionally mono- or polysubstituted phenylalkyl, having 1 to 4 carbon atoms in the alkyl part and being straight-chain or branched in the alkyl part, the substituents being in the phenyl part and being identical or different and suitable phenyl substituents being those mentioned in the case of $R^2$, $R^4$ represents in each case straight-chain or branched alkyl, alkenyl, alkinyl, halogenoalkyl or halogenoalkenyl in each case having up to 8 carbon atoms and, if appropriate, up to 17 halogen atoms, additionally represents in each case straight-chain or branched alkoxyalkyl or alkylthioalkyl in each case having 1 to 4 carbon atoms in the individual alkyl parts, cycloalkyl having 3 to 7 carbon atoms, or optionally mono- or polysubstituted phenylalkyl, having 1 to 4 carbon atoms in the alkyl part and being straight-chain or branched in the alkyl part, the substituents being in the phenyl part and being identical or different and suitable phenyl substituents being those mentioned in the case of $R^2$, and in addition also represents hydrogen in the case where $R^3$ does not simultaneously represent unsubstituted alkyl, or $R^3$ and $R^4$, together with the nitrogen atom to which they are bound, represent a 3- to 7-membered saturated heterocycle, which can contain up to 2 further heteroatoms, particularly nitrogen, oxygen and/or sulphur, Ar represents in each case optionally mono- or polysubstituted phenyl, 2-pyridyl, 3-pyridyl or 4-pyridyl, the substituents being identical or different and suitable substituents in each case being: cyano, nitro, halogen, in each case straight-chain or branched alkyl, alkoxy or alkoxycarbonyl, in each case having 1 to 4 carbon atoms, in each case straight-chain or branched halogenoalkyl or halogenoalkoxy in each case having 1 to 4 carbon atoms and 1 to 9 identical or different halogen atoms, or a —S(O)$_p$—R$^6$ radical, and n represents a number 0, 1 or 2, where $R^6$ represents amino, and also in each case straight-chain or branched alkyl, alkylamino, dialkylamino or halogenoalkyl, in each case having up to 4 carbon atoms in the individual alkyl parts and, in the case of halogenoalkyl, having up to 9 identical or different halogen atoms, and p represents a number 0, 1 or 2.

Particularly preferred 1-arylpyrazoles of the formula (I) are those in which $R^1$ represents hydrogen, methyl, ethyl, n- or i-propyl and trifluoromethyl, $R^2$ represents methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, cyclopropyl, cyclobutyl, cyclopentyl, cyclohexyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorodibromomethyl, difluorobromomethyl, fluorochlorobromomethyl, chloroallyl, fluoroallyl, chlorobutenyl, fluorobutenyl, dichloroallyl, fluorochloroallyl, dichlorobutenyl, difluoroallyl, bromoallyl, methoxymethyl, methoxyethyl, methoxypropyl, ethoxymethyl, ethoxyethyl, methylthiomethyl, methylsulphinylmethyl, methylsulphonylether, methylthioethyl, methylthiopropyl, methylsulphinylethyl, methylsulphonylmethyl or in each case optionally monoto trisubstituted phenyl, benzyl or phenylethyl, the substituents being identical or different and suitable phenyl substituents in each case being: fluorine, chlorine, bromine, iodine, cyano, nitro, methyl, ethyl, methoxy, methylthio, trifluoromethyl, methylsulphinyl, methylsulphonyl, trifluoromethoxy, trifluoromethylthio, trifluoromethylsulphinyl or trifluoromethylsulphonyl, $R^3$ represents methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, cyclopropyl, cyclobutyl, cyclopentyl, cyclohexyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorodibromomethyl, difluorobromomethyl, fluorochlorobromomethyl, chloroallyl, fluoroallyl, chlorobutenyl, fluorobutenyl, dichloroallyl, fluorochloroallyl, dichlorobutenyl, difluoroallyl, bromoallyl, methoxymethyl, methoxyethyl, methoxypropyl, ethoxymethyl, ethoxyethyl, methylthiomethyl, methylthioethyl, methylthiopropyl, ethylthiomethyl, ethylthioethyl or in each case optionally mono- to trisubstituted benzyl or phenylethyl, the substituents being in the phenyl part and being identical or different and suitable phenyl substituents being those mentioned in the case of $R^2$, $R^4$ represents methyl, ethyl, n- or i-propyl, n-i-, s- or t-butyl, n- or i-pentyl, n- or i-hexyl, allyl, n- or i-butenyl, n- or i-pentenyl, propargyl, n- or i-butinyl, cyclopropyl, cyclobutyl, cyclopentyl, cyclohexyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorodibromomethyl, difluorobromomethyl, fluorochlorobromomethyl, chloroallyl, fluoroallyl, chlorobutenyl, fluorobutenyl, dichloroallyl, fluorochloroallyl, dichlorobutenyl, difluoroallyl, bromoallyl, methoxymethyl, methoxyethyl, methoxypropyl, ethoxymethyl, ethoxyethyl, methylthiomethyl, methylthioethyl, methylthiopropyl, ethylthiomethyl, ethylthioethyl or in each case optionally mono- to trisubstituted benzyl or phenylethyl, the substituents being in the phenyl part and being identical or different and suitable phenyl substituents being those mentioned in the case of $R^2$, and, in addition, also represents hydrogen in the case where $R^3$ does not simultaneously represent unsubstituted alkyl, or $R^3$ and $R^4$, together with the nitrogen atom to which they are bound, represent pyrrolidinyl, piperidinyl, perhydroazepinyl or morpholinyl, Ar represents optionally mono- to pentasubstituted phenyl, the substituents being identical or different, or optionally mono- to tetrasubstituted 2-pyridyl, the substituents being identical or different and suitable substituents in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an —S(O)$_p$—R$^6$ radical, and n represents a number 0, 1 or 2, where R$^6$ represents amino, methylamino, ethylamino, dimethylamino, diethylamino, fluorodichloromethyl, difluoromethyl, tetrafluoroethyl, trifluorochloroethyl, trichloromethyl, trichloroethyl, trifluoromethyl, methyl or ethyl, and p represents a number 0, 1 or 2.

Apart from the compounds mentioned in the preparation examples, the following 1-aryl-pyrazoles of the general formula (I) may be mentioned individually:

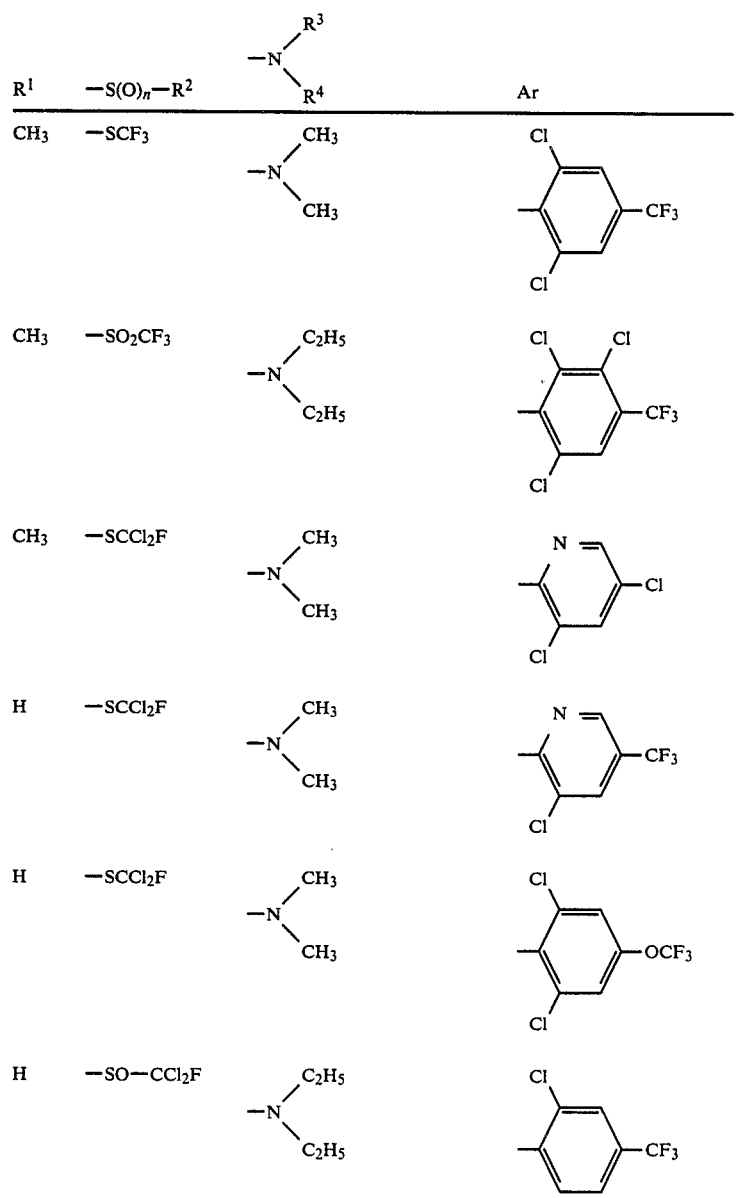

-continued

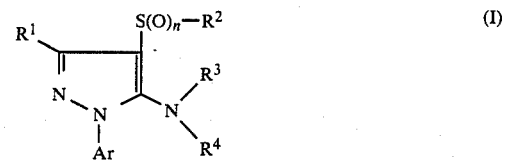

| $R^1$ | $-S(O)_n-R^2$ | $-N\begin{smallmatrix}R^3\\R^4\end{smallmatrix}$ | Ar |
|---|---|---|---|
| $CH_3$ | $-SO_2-CCl_2F$ | $-N(CH_3)(C_2H_5)$ | 2-Cl, 4-OCF$_3$ phenyl |
| $C_2H_5$ | $-S-CF_3$ | pyrrolidin-1-yl | 2-Cl, 3-Br, 4-CF$_3$ phenyl |
| H | $-SCF_3$ | pyrrolidin-1-yl | 3-Cl, 5-CF$_3$ pyridin-2-yl |
| H | $-S-CH_3$ | piperidin-1-yl | 2,6-diCl, 4-CF$_3$ phenyl |
| $CH_3$ | $-S-CH_3$ | morpholin-4-yl | 2-Cl, 4-CF$_3$ phenyl |
| $CH_3$ | $-SO_2-CH_3$ | pyrazolidin-1-yl | 2-Cl, 4-OCF$_3$ phenyl |
| $CH_3$ | $-SO_2-C_2H_5$ | $-N(CH_3)_2$ | 2,6-diCl, 4-CF$_3$ phenyl |
| H | $-S-CClF_2$ | $-NH-CH_2-CH_2OCH_3$ | 2,6-diCl, 4-CF$_3$ phenyl |

-continued $$\begin{array}{c} R^1 \quad S(O)_n-R^2 \\ \diagup\!\!\!\diagdown \\ N \quad N\diagdown \begin{array}{c} R^3 \\ R^4 \end{array} \\ | \\ Ar \end{array} \quad (I)$$

| $R^1$ | $-S(O)_n-R^2$ | $-N\begin{array}{c}R^3\\R^4\end{array}$ | Ar |
|---|---|---|---|
| CH₃ | —SO₂—CClF₂ | —NH—CH₂—SCH₃ | 3,5-dichloropyridin-2-yl |
| H | —SO₂CF₃ | —N(CH₃)₂ | 2,6-dichloro-4-(trifluoromethyl)phenyl |
| H | —SCF₃ | —N(CH₃)₂ | 2-chloro-4-(trifluoromethyl)phenyl |
| H | —SCF₃ | —N(CH₃)₂ | 3-chloro-5-(trifluoromethyl)pyridin-2-yl |
| CH₃ | —SO₂CF₃ | —N(CH₃)₂ | 2,6-dichloro-4-(trifluoromethyl)phenyl |
| H | —SO₂CF₃ | morpholin-4-yl | 2,6-dichloro-4-(trifluoromethyl)phenyl |
| H | —SO₂CF₃ | —NH—CH₂—CH₂—OCH₃ | 2,6-dichloro-4-(trifluoromethyl)phenyl |
| H | —SO₂CF₃ | —N(CH₂CH₂OCH₃)₂ | 2-chloro-4-(trifluoromethoxy)phenyl |

-continued

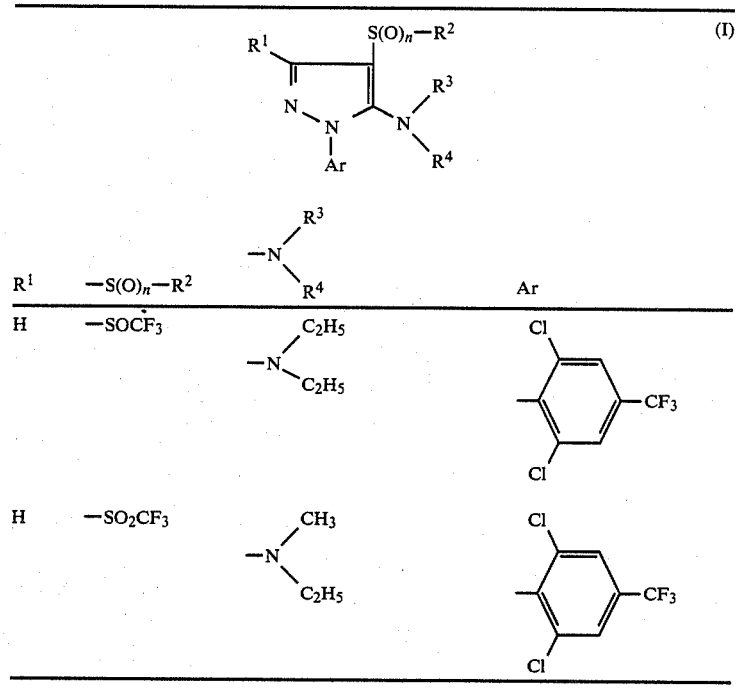

| $R^1$ | $-S(O)_n-R^2$ | $-N\begin{smallmatrix}R^3\\R^4\end{smallmatrix}$ | Ar |
|---|---|---|---|
| H | $-SOCF_3$ | $-N\begin{smallmatrix}C_2H_5\\C_2H_5\end{smallmatrix}$ | 2,6-dichloro-4-trifluoromethylphenyl |
| H | $-SO_2CF_3$ | $-N\begin{smallmatrix}CH_3\\C_2H_5\end{smallmatrix}$ | 2,6-dichloro-4-trifluoromethylphenyl |

If, for example, 5-bromo-1-(2,6-dichloro-4-trifluoromethyl-phenyl)-4-fluorodichloromethylsulphonyl-pyrazole and 2-methoxyethylamine are used as starting materials, then the course of the reaction of the process (a) according to the invention can be represented by the following equation:

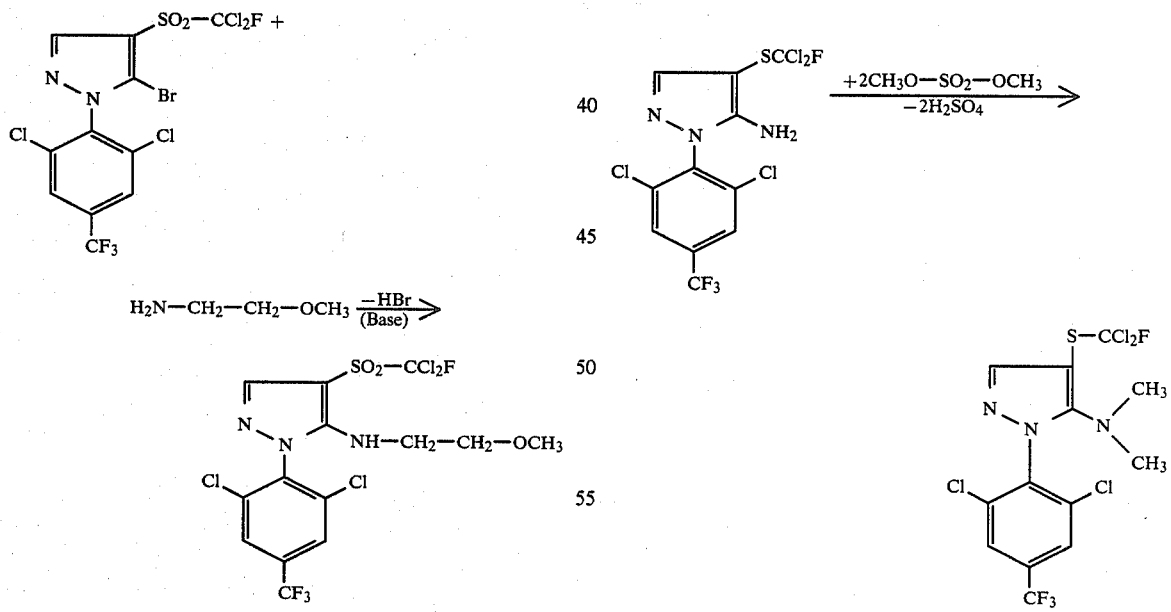

If, for example, 5-amino-1-(2,6-dichloro-4-trifluoromethyl-phenyl)-4-fluorodichloromethylthio-pyrazole and dimethyl sulphate are used as starting materials, then the course of the reaction of the process (b) according to the invention can be represented by the following equation:

If, for example, 3-methyl-5-dimethylamino-1-(2-chloro-4-trifluoromethyl-phenyl)-pyrazole and trifluoromethylsulphenyl chloride are used as starting materials, then the course of the reaction of the process (c) according to the invention can be represented by the following equation:

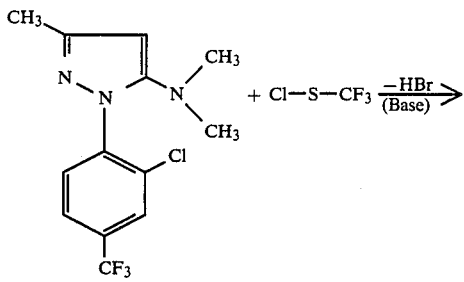

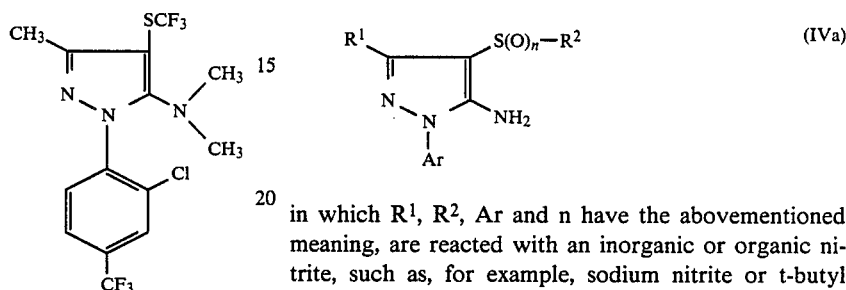

If, for example, 5-diethylamino-3-methyl-4-trifluoromethylthio-1-(2,4,6-trichlorophenyl)-pyrazole is used as starting material and 3-chloroperbenzoic acid is used as oxidant, then the course of the reaction of the process (d) according to the invention can be represented by the following equation:

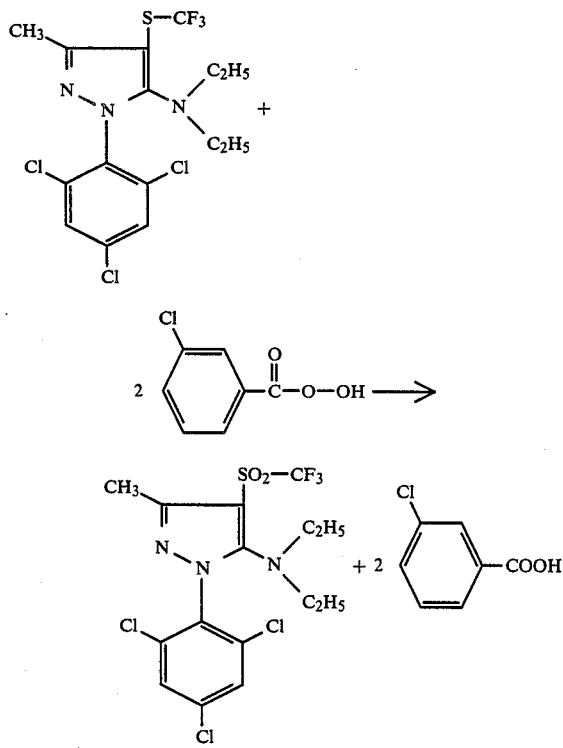

The 5-halogeno-1-aryl-pyrazoles which are required as starting materials for carrying out the process (a) according to the invention are generally defined by the formula (II). In this formula (II), $R^1$, $R^2$, Ar and n preferably represent those radicals and indices which have already been mentioned in connection with the description of the substances, according to the invention, of the formula (I) as being preferred for these indices and substituents.

$Hal^1$ preferably represents chlorine or bromine.

The 5-halogeno-1-aryl-pyrazoles of the formula (II) are the subject of commonly assigned U.S. application Ser. No. 893,133 filed Aug. 4, 1986, now pending, corresponding to German Patent Application P No. 3,529,829 of Aug.21, 1985.

They are are obtained, for example, when 5-amino-1-aryl-pyrazoles of the formula (IVa), $$R^1 \underset{N-N}{\underset{|}{\parallel}} \overset{S(O)_n-R^2}{\underset{NH_2}{\diagdown}} \quad \text{(IVa)}$$
$$\text{Ar}$$

in which $R^1$, $R^2$, Ar and n have the abovementioned meaning, are reacted with an inorganic or organic nitrite, such as, for example, sodium nitrite or t-butyl nitrite, in the presence of a halogenating agent, such as, for example, hydrochloric acid or bromoform, at temperatures between 0° C. and +80° C.

The amines which are furthermore required as scarting materials for carrying out the process (a) according to the invention and for the synthesis of the precursors of the formula (VIb) are generally defined by the formula (III). In this formula (III), $R^3$ and $R^4$ preferably represent those radicals which have already been mentioned in connection with the description of the substances, according to the invention, of the formula (I) as being preferred for these substituents.

The amines of the formula (III) are generally known compounds of organic chemistry.

The 5-amino-1-aryl-pyrazoles which are required as starting materials for carrying out the process (b) according to the invention are generally defined by the formula (IV). In this formula (IV), $R^1$, $R^2$, $R^4$, Ar and n preferably represent those radicals and indices which have already been mentioned in connection with the description of the substances, according to the invention, of the formula (I) as being preferred for these indices and substituents.

Some of the 5-amino-1-aryl-pyrazoles of the formula (IV), like the 5-amino-1-aryl-pyrazoles of the formula (IVa) which are required for the preparation of the precursors of the formula (II), are known (cf., for example, Farmaco. Ed. Sci. 26, p. 276–293 [1971], DE-OS (German Published Specification) No. 3,402,308, or Mycopathologica 74, p. 7–14 [1981]), some are subject of commonly assigned U.S. application Ser. No. 858,475, filed Apr. 30, 1986, now pending, corresponding to German Patent Application P No. 3,517,843 of May 16, 1985, and some are compounds according to the invention and can be obtained using the process (a), (b), (c) or (d) according to the invention.

The previously-described 5-amino-1-aryl-pyrazoles of the formula (IV) or (IVa) are obtained analogously to known processes, for example when 4-thiocyanato-5-aminopyrazoles of the general formula (IX),

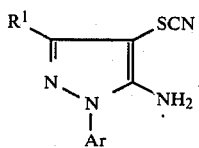    (IX)

in which R¹ and Ar have the abovementioned meaning, or bis-(pyrazolyl) disulphides of the formula (X),

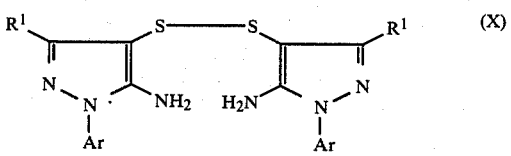    (X)

in which R¹ and Ar have the abovementioned meaning, are reacted with halides of the formula (XI)

    (XI)

in which
R² has the abovementioned meaning, and
Hal³ represents halogen, particularly chlorine, bromine or iodine,
if appropriate in the presence of a diluent, such as, for example, methanol or ethanol, and if appropriate in the presence of a reducing agent, such as, for example, sodium borohydride or sodium dithionite, and if appropriate in the presence of a base, such as, for example, sodium hydroxide or potassium carbonate, at temperatures between 20° C. and 90° C., or when 4-unsubstituted 5-amino-pyrazoles of the formula (VIa),

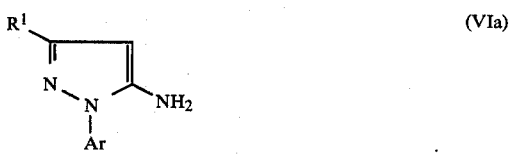    (VIa)

in which R¹ and Ar have the abovementioned meaning, are reacted with sulphenyl halides of the formula (VII),

    (VII)

in which
R² has the abovementioned meaning and
Hal² represents halogen, particularly fluorine, chlorine, bromine or iodine,
analogously to the carrying out of the process (c) according to the invention, if appropriate in the presence of a diluent, such as, for example, dichloromethane, and if appropriate in the presence of an acid acceptor, such as, for example, pyridine, at temperatures between 0° C. and 50° C., and, if appropriate, subsequently oxidizing the 5-amino-pyrazoles of the formula (IVb),

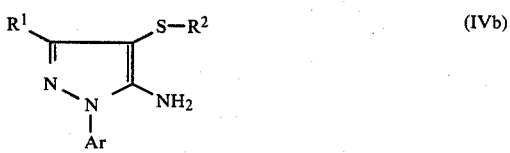    (IVb)

in which R¹, R² and Ar have the abovementioned meaning, which can be thus obtained on the sulphur of the sulphenyl group in the 4-position position of the pyrazole ring using oxidants of the formula (VIII),

    (VIII)

in which R⁵ represents hydrogen or in each case optionally substituted alkanoyl or aroyl, preferably hydrogen, acetyl, propionyl, trifluoroacetyl or optionally substituted benzoyl, such as, for example, 3-chlorobenzoyl or 4-nitrobenzoyl, analogously to the carrying out of the process (d) according to the invention, if appropriate in the presence of a diluent, such as, for example, dichloromethane, if appropriate in the presence of a catalyst, such as, for example, ammonium molybdate, and also if appropriate in the presence of an acid acceptor, such as, for example, sodium carbonate or sodium bicarbonate, at temperatures between 0° C. and 50° C.

5-Amino-1-aryl-pyrazoles of the formula (IVd),

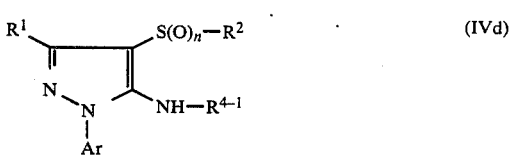    (IVd)

in which
R¹, R², Ar and n have the abovementioned meaning and
R⁴⁻¹ represents the same radicals as R⁴, with the exception of the hydrogen radical,
are obtained either by reaction of the precursors of the formula (II),

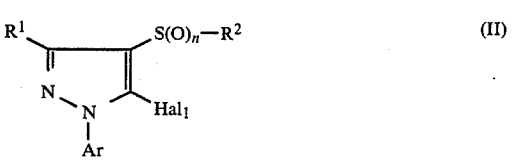    (II)

in which R¹, R², Ar, Hal¹ and n have the abovementioned meaning, with amines of the formula (IIIa),

    (IIIa)

in which R⁴⁻¹ has the abovementioned meaning, analogously to the carrying out of the process (a) according to the invention, or by reaction of the precursors of the formula (IVa),

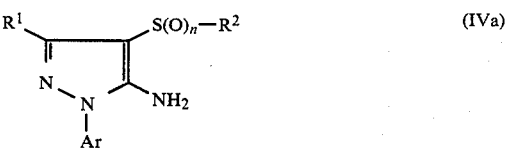    (IVa)

in which
R¹, R², Ar and n have the abovementioned meaning, with alkylating agents of the formula (Va),

    (Va)

in which R⁴⁻¹ and E¹ have the abovementioned meaning, analogously to the carrying out of the process (b) according to the invention.

The amines of the formula (IIIa) and the alkylating agents of the formula (Va) are generally known compounds of organic chemistry.

Some of the 4-thiocyanato-5-aminopyrazoles of the formula (IX) are known (cf., for example, Farmaco Ed. Sci. 38, p. 274–282 [1983]). They are obtained, for example, when 4-unsubstituted 5-aminopyrazoles of the formula (VIa),

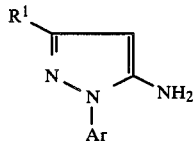

(VIa)

in which $R^1$ and Ar have the abovementioned meaning, are reacted with ammonium thiocyanate in the presence of bromine and acetic acid at temperatures between $-20°$ C. and $+20°$ C.

The bis-(pyrazole) disulphides of the formula (X), are not yet known. They are obtained when the 4-thiocyanato-5-amino-pyrazoles, of the formula (IX), described above are reacted with aqueous hydrochloric acid, if appropriate in the presence of a diluent, such as, for example, ethanol, at temperatures between 20° C. and 120° C.

The halides of the formula (XI) are generally known compounds of organic chemistry.

Some of the 4-unsubstituted 5-aminopyrazoles of the formula (VIa) are known (cf., for example, J. Org. Chem. 36, p. 2972–2974 [1971] or J. Heterocyclic Chemistry 7, p. 345–349 [1970]; C.A. 62: 13137c).

They are obtained, for example, when arylhydrazines of the formula (XII),

(XII)

in which Ar has the abovementioned meaning, are reacted with acrylonitrile derivatives of the formula (XIII),

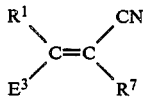

(XIII)

in which
$R^1$ has the abovementioned meaning,
$R^7$ represents hydrogen or alkoxycarbonyl and
$E^3$ represents halogen, hydroxy, alkoxy, amino or dialkylamino, either initially in a 1st stage, if appropriate in the presence of a diluent, such as, for example, ethanol or glacial acetic acid, and if appropriate in the presence of a reaction auxiliary, such as, for example, sodium acetate, at temperatures between $-20°$ C. and $+20°$ C. to form the arylhydrazine derivatives of the formula (XIV),

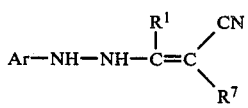

(XIV)

in which Ar, $R^1$ and $R^7$ have the abovementioned meaning, and cyclizing this in a 2nd stage, if appropriate in the presence of a diluent, such as, for example, ethylene glycol monoethyl ether, at temperatures between $+50°$ C. and $+150°$ C., or directly cyclizing it in one reaction step without isolation of the intermediate of the formula (XIV), if appropriate in the presence of a diluent, such as, for example, ethylene glycol monoethyl ether, at temperatures between $+50°$ C. and $+150°$ C., to form the 5-aminopyrazoles of the formula (XV),

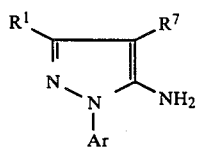

(XV)

in which
$R^1$, $R^7$ and Ar have the abovementioned meaning, and, in the case where $R^7$ represents alkoxycarbonyl, saponifying and decarboxylating the compounds of the formula (XV) in a generally conventional fashion, if appropriate in the presence of a diluent, such as, for example, ethanol or isopropanol, and if appropriate in the presence of a catalyst, such as, for example, hydrobrom acid, at temperatures between 50° C. and 150° C.

The arylhydrazines of the formula (XII) are known (cf., for example, U.S. Pat. Specification No. 4,127,575; U.S. Patent Specification No. 3,609,158; DE-OS (German Published Specification) No. 2,558,399; J. Chem. Soc. C, 1971, p. 167–174) or they can be prepared in a simple analogous fashion by processes which are known in principle (cf. HoubenWeyl "Methoden der organischen Chemie [Methods of Organic Chemistry]" volume X, 2 p. 203, Thieme Verlag Stuttgart, 1967).

The acrylonitrile derivatives of the formula (XIII) are generally known compounds of organic chemistry.

The alkylating agents which are furthermore required for carrying out the process (b) according to the invention and for the synthesis of the precursors of the formula (VIb) are generally defined by the formula (V). In this formula (V), $R^3$ preferably represents those radicals which have already been mentioned in connection with the description of the substances, according to the invention, of the formula (I) as being preferred for these substituents.

$E^1$ preferably represents halogen, particularly chlorine, bromine or iodine, or in each case optionally substituted alkylsulphonyloxy, alkoxysulphonyloxy or arylsulphonyloxy, such as, for example, methoxysulphonyloxy or p-tolylsulphonyloxy.

The alkylating agents of the formula (V) are generally known compounds of organic chemistry.

The 4-unsubstituted 1-aryl-pyrazoles which are required as starting materials for carrying out the process (c) according to the invention are generally defined by the formula (VI). In this formula (VI), $R^1$, $R^3$, $R^4$ and Ar preferably represent those radicals which have already been mentioned in connection with the description of the substances, according to the invention, of the formula (I) as being preferred for these substituents.

Some of the 4-unsubstituted 1-aryl-pyrazoles of the formula (VI) are known (cf., for example, Heterocycles 4, p. 1921–1932, [1976]; Bull. Soc. Chim. France, 1970, p. 4436–4438; Gazz. Chim. Ital. 97, p. 410–420 [1967]; GDR Patent Specification No. 208,466 of 02.05.1984, or CA 101, 230514d].

4-unsubstituted 1-aryl-pyrazoles of the formula (VIb),

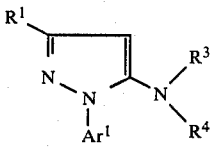
(VIb)

in which
R¹, R³ and R⁴ have the abovementioned meaning and Ar¹ represents disubstituted phenyl or optionally substituted pyridyl,
are not yet known.

They are obtained [analogously to known processes, as are the known compounds of the formula (VI)], for example, when 4-unsubstituted 1-aryl-pyrazoles of the formula (VIa¹),

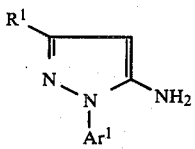
(VIa¹)

in which R¹ and Ar¹ have the abovementioned meaning, are alkylated using alkylating agents of the formula (V)

$$R^3\text{-}E^1 \quad (V)$$

in which R³ and E¹ have the abovementioned meaning, analogously to the carrying out of the process (b) according to the invention, if appropriate in the presence of a diluent, such as, for example, acetonitrile, and if appropriate in the presence of an acid acceptor, such as, for example, potassium carbonate, at temperatures between 0° C. and 120° C., or when 5-halogeno-1-aryl-pyrazoles of the formula (XVI)

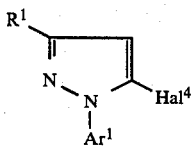
(XVI)

in which
R¹ and Ar¹ have the abovementioned meaning and
Hal⁴ represents halogen, particularly chlorine or bromine, are reacted with amines of the formula (III),

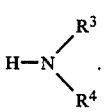
(III)

in which R³ and R⁴ have the abovementioned meaning, analogously to the carrying out of the process (a) according to the invention, if appropriate in the presence of a diluent, such as, for example, dioxane, and if appropriate in the presence of an acid acceptor, such as, for example, triethylamine, at temperatures between +20° C. and +120° C.

The 5-halogeno-1-aryl-pyrazoles of the formula (XVI) are known (cf., for example, Bull. Soc. Chim. France 1966, p. 3744–52; Canad. J. Chem. 46, p. 1079–1091 [1968]; Bull. Soc. Chim. France 1968, p. 5019–5029), or can be obtained in a simple, analogous fashion by known processes (cf., for example, Khim Geterotsikl. Soedin. 1967, p. 130–134; Tetrahedron Letters 1968, p. 1949–1951; J. Heterocycl. Chem. 18, p. 9–14 [1981]).

The sulphenyl halides which are furthermore required as starting materials for carrying out the processs (c) according to the invention and for the synthesis of the precursors of the formula (IVb) are generally defined by the formula (VII). In this formula (VII), R² preferably represents those radicals which have already been mentioned in connection with the description of the substances, according to the invention, of the formula (I) as being preferred for these substituents.

Hal² preferably represents fluorine, chlorine, bromine or iodine.

The sulphenyl halides of the formula (VII) are generally known compounds of organic chemistry.

The 1-aryl-pyrazoles which are required as starting materials for carrying out the process (d) according to the invention are generally defined by the formula (Ia). In this formula (Ia), R¹, R², R³, R⁴ and Ar preferably represent those radicals which have already been mentioned in connection with the description of the substances, according to the invention, of formula (I) as being preferred for these substituents.

The 1-aryl-pyrazoles of the formula (Ia) are compounds according to the invention and can be obtained with the aid of the process (a), (b) or (c) according to the invention.

The oxidants which are furthermore required as starting materials for carrying out the process (d) according to the invention and for the synthesis of the precursors of the formula (IV) are generally defined by the formula (VIII). In this formula (VIII), R⁵ preferably represents hydrogen, acetyl or optionally substituted benzoyl, such as, for example, 3-chlorobenzoyl or 4-nitrobenzoyl.

The oxidants of the formula (VIII) are likewise generally known compounds of organic chemistry.

Suitable diluents for carrying out the preparation process (a) are inert organic solvents. These include, in particular, aliphatic alicyclic or aromatic, optionally halogenated, hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

If appropriate, the process (a) according to the invention can be carried out in the presence of a suitable acid acceptor. Suitable as such are all conventional inorganic or organic bases. These include, for example, alkali metal hydroxides, such as sodium hydroxide or potassium hydroxide, alkali metal carbonates, such as sodium carbonate, potassium carbonate or sodium bicarbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is also possible to use an appropriate excess of the amine of the formula (III) employed as coreactant partner simultaneously as an acid acceptor.

The reaction temperatures can be varied within a relatively wide range when the process (a) according to the invention is carried out. In general, the process is carried out at temperatures between −20° C. and +200° C., preferably at temperatures between 0° C. and +150° C.

To carry out the process (a) according to the invention, 1.0 to 10.0 mols preferably 1.0 to 5.0 mols, of amines of the formula (III) are, in general, employed per mol of 5-halogeno-1-aryl-pyrazole of the formula (II). The reaction is carried out, and the reaction products of the formula (I) are worked up and isolated by generally conventional processes.

Suitable diluents for carrying out the process (b) are inert organic solvents. These include, in particular, aliphatic or aromatic, optionally halogenated, hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

The process (b) according to the invention can, if appropriate, alternatively be carried out in a twophase system, such as, for example, water/toluene or water/dichloromethane, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}/C_{15}$-alkylammonium chloride, trimethylbenzyl-ammonium methylsulphate, dimethyl-$C_{12}/C_{14}$-alkylbenzylammonium chloride, tetrabutylammonium hydroxide, 15-crown-5, 18-crown-6, triethylbenzylammonium chloride, and trimethylbenzylammonium chloride.

Suitable acid binders for carrying out the preparation process (b) are all inorganic and organic bases which can conventionally be used. Alkali metal hydrides, hydroxides, amides, alcoholates, carbonates or bicarbonates, such as, for example, sodium hydride, sodium amide, sodium methylate, sodium hydroxide, sodium carbonate or sodium bicarbonate, or alternatively tertiary amines, such as, for example, triethylamine, N,N-dimethylaniline, pyridine, 4-(N,N-dimethylamino)pyridine, diazabicyclooctane (DABCO), diazabicyclononene (DBN) or diazabicycloundecene (DBU), are preferably used.

The reaction temperatures can be varied within a relatively wide range when the preparation process (b) is carried out. In general, the process is carried out at temperatures between −20° C. and +150° C., preferably between 0° C. and +100° C.

To carry out the preparation process (b), 1.0 to 20.0 mols, preferably 1.0 to 15.0 mols of alkylating agent of the formula (V) and, if appropriate, 1.0 to 3.0 mols, preferably 1.0 to 2.0 mols, of acid acceptor and also 0.01 to 1.0 mol of phase transfer catalyst are, in general, employed per mol of 5-amino-1-aryl-pyrazole of the formula (IV). The reaction is carried out, and the reaction products of formula (I) are worked up and isolated in a generally conventional fashion.

Suitable diluents for carrying out the process (c) are inert organic solvents. These include, in particular, aliphatic or aromatic, optionally halogenated, hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

The process (c) according to the invention is, if appropriate, carried out in the presence of an acid acceptor. Suitable as such are all conventional inorganic or organic bases. These include, for example, alkali metal hydroxides, such as sodium hydroxide or potassium hydroxide, alkali metal carbonates, such as sodium carbonate, potassium carbonate or sodium bicarbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperatures can be varied within a relatively wide range when the process (c) according to the invention is carried out. In general, the process is carried out at temperatures between −20° C. and +120° C., preferably at temperatures between 0° C. and +50° C.

To carry out the process (c) according to the invention, 1.0 to 2.5 mols, preferably 1.0 to 1.5 mols, of sulphenyl halide of the formula (VII) and 1.0 to 2.5 mols, preferably 1.0 to 1.5 mols, of acid acceptor are, in general, employed per mol of 4-unsubstituted 1-aryl-pyrazole of the formula (VI). The reaction is carried out, and the reaction products of the formula (Ia) are worked up and isolated by generally conventional processes.

Suitable diluents for carrying out the-process (d) according to the invention are likewise inert organic solvents.

Hydrocarbons, such as benzine, benzene, toluene, hexane or petroleum ether; chlorinated hydrocarbons, such as dichloromethane, 1,2-dichloroethane, chloroform, carbon tetrachloride or chlorobenzene; ethers, such as diethyl ether, dioxane or tetrahydrofuran; carboxylic acids, such as acetic acid or propionic acid, or dipolar aprotic solvents, such as acetonitrile, acetone, ethyl acetate or dimethylformamide, are preferably used.

The process (d) according to the invention can, if appropriate, be carried out in the presence of an acid acceptor. Suitable as such are all organic and inorganic acid acceptors which can conventionally be used. Alkaline earth metal or alkali metal hydroxides, acetates or carbonates, such as, for example, calcium carbonate, sodium hydroxide, sodium acetate or sodium carbonate, are preferably used.

The process (d) according to the invention can, if appropriate, be carried out in the presence of a suitable catalyst. Suitable as such are all catalysts which are conventional for such sulphur oxidations. Examples which may be mentioned in this connection are heavy metal catalysts, such as ammonium molybdate.

The reaction temperatures can be varied within a relatively wide range when the process (d) according to the invention is carried out. In general, the process is carried out at temperatures between −20° C. and +70°

C., preferably at temperatures between 0° C. and +50° C.

To carry out the process (d) according to the invention, 0.8 to 1.2 mols, preferably equimolar amounts, of oxidants of the formula (VIII) are, in general, employed per mol of 1-aryl-pyrazole of the formula (Ib) when it is desired to interrupt the oxidation of the sulphur at the sulphoxide stage. For oxidation to the sulphone, 1.8 to 3.0 mols, preferably double the molar amounts, of oxidants of the formula (VIII) are, in general, employed per mol of 1-aryl-pyrazole of the formula (Ib). The reaction is carried out, and the final products of the formula (Ib) are worked up and isolated by conventional processes.

The active compounds are suitable for combating animal pests, in particular insects, arachnida and nematodes, which are encountered in agriculture, in forestry, in the protection of stored products and of materials, and in the hygiene field, and have good plant tolerance and favourable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber*. From The order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp.. From the order of the Anoplura, for example, *Phylloxera vastatrix*, Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., Earias insulana, Heliothis spp., *Laphygma exigua, Mamestra brassicae, Panolis flammea, Prodenia litura*, Spodoptera spp., Trichoplusiani, Caprocapsa pomonella, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus*, Oscinella frit, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp. From the order of the Arachnida, for example, *Scorpio maurus* and Latrodectus mactans. From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp. and Trichodorus spp..

The active compounds according to the invention are active not only against plant, hygiene and stored product pests, but also, in the veterinary medicine sector, against animal parasites (ectoparasites), such as scaly ticks, argasidae, scab mites, trombidae, flies (stinging and sucking), parasitic fly larvae, lice, hair lice, bird lice and fleas.

They are active against normally sensitive and resistant species and strains, as well as against all parasitic and non-parasitic stages of development of the ectoparasites.

The active compounds according to the invention have a strong insecticidal and acaricidal action. They can be employed particularly against insects which are harmful to plants, such as, for example, against the larvae of cabbage moth (*Plutella maculipennis*) or against the larvae of the mustard beetle (*Phaedon cochleariae*), and also against mites which damage plants, such as, for example, against the two-spotted spider mite (*Tetranychus urticae*). In addition, they are suitable for combating soil insects and can be employed, for example, for combating *Phorbia antiqua* grubs. A notable root-systemic action, for example against *Phaedon cochleariae* grubs and *Myzus persicae*, should be emphasized.

In addition, the active compounds, of the formula (I), which can be used according to the invention have a high activity against hygiene pests and stored product pests and can be employed, for example, for combating German cockroaches (*Blattella germanica*) or for combating the grain weevil (*Sitophilus granarius*) In addition, the active compounds according to the invention can be particularly successfully used for combating pests which live parasitically on warm-blooded animals, such as, for example, against scab mites (*Psoroptes ovis*), against stable flies (*Stomoxys calcitrans*) or against the face fly (*Musca autumnalis*).

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound conceptration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds which can be used according to the invention are also suitable for combating insects, midges, ticks etc. in the sectors of animal husbandry and cattle breeding; better results, for example higher milk production, greater weight, more attractive animal pelt, longer life etc., can be achieved by combating the pests.

The application of the active compounds which can be used according to the invention occurs in this sector in a known fashion, such as by oral application in the form of, for example, tablets, capsules, potions, granules, by means of dermal or external application in the form of, for example, dipping, spraying, pouring-on, spotting-on and dusting, as well as by means of parenteral application in the form, for example, of injection, and, furthermore, by means of the feed-through process. In addition, application as molded articles (collar, ear tag) is also possible.

The biological effectiveness of the compounds according to the invention will be explained with reference to the examples below.

PREPARATION EXAMPLES

EXAMPLE 1

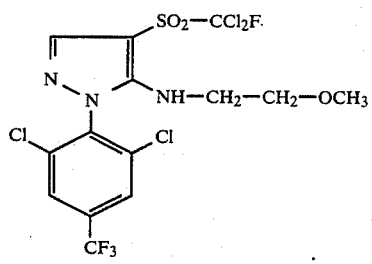

(Process a)

32 g (0.06 mol) of 5-bromo-4-dichlorofluoromethanesulphonyl-1-(2,6-dichloro-4-trifluoromethyl-phenyl)-pyrazole and 40 g (0.53 mol) of 2-methoxyethylamine are dissolved in 100 ml of dioxane and stirred for 24 hours at 80° C. After cooling, the reaction mixture is poured into water and subsequently extracted with toluene. The toluene phase is washed several times with water, dried over sodium sulphate and concentrated in vacuo. The crystalline residue is recrystallized from ligroin.

17 g (55% of theory) of 4-dichlorofluoromethanenesulphonyl-5-(2-methoxyethyl)-amino-1-(2,6-dichloro-4-trifluoromethyl-phenyl)-pyrazole of melting point 91° C.-94° C. are obtained.

Preparation of the starting compound

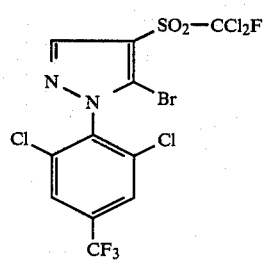

98 g (0.21 mol) of 5-amino-4-dichlorofluoromethanesulphonyl-1-(2,6-dichloro-4-trifluoromethyl-phenyl)pyrazole are added in portions to a solution of 72 g of tertiary butyl nitrite (0.7 mol) in 400 ml of bromoform with stirring and cooling. The temperature is maintained between 25° C. and 30° C. After stirring for 12 hours, the solution is concentrated in a rotary evaporator and the residue is crystallized using petroleum ether.

95.4 g (85% of theory) of 5-bromo-4-dichlorofluoromethanesulphonyl)-1-(2,6-dichloro-4-trifluoromethylphenyl)-pyrazole of melting point 97° C.-98° C. are obtained.

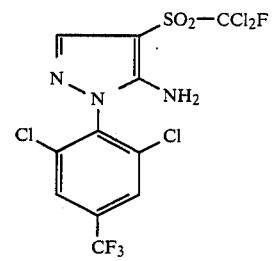

32 g (0.17 mol) of approximately 90 per cent strength m-chloroperbenzoic acid are added in portions to 30 g (0.07 mol) of 5-amino-4-dichlorofluoromethanesulphenyl-1-(2,6-dichloro-4-trifluoromethyl-phenyl)-pyrazole in 200 ml of dichloromethane, stirred for about 30 hours at room temperature and filtered, and the filtrate is washed successively with saturated aqueous sodium bicarbonate solution, saturated aqueous sodium thiosulphate solution and again with saturated aqueous sodium bisulphate solution, dried over magnesium sulphate and freed of solvent in vacuo.

26.3 g (81.5% of theory) of 5-amino-4-dichlorofluoromethylsulphonyl-1-(2,6-dichloro-4-trifluoromethylphenyl)-pyrazole of melting point 132° C.-135° C. are obtained.

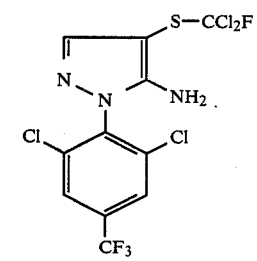

10 g (0.034 mol) of 5-amino-1-(2,6-dichloro-4-trifluoromethylphenyl)-pyrazole are dissolved in 50 ml of glacial acetic acid and 6.1 g (0.036 mol) of dichlorofluoromethanesulphenyl chloride are added dropwise at room temperature. The temperature increases to about 40° C. The reaction mixture is stirred for 2 hours and then introduced into a mixture of 200 ml of water and 50 ml of dichloromethane. The organic phase is separated off, and the aqueous phase is extracted with twice 20 ml of dichloromethane. The combined organic phases are washed successively with sodium bicarbonate solution and sodium chloride solution, dried over magnesium sulphate and concentrated in vacuo.

13.6 g (94% of theory) of 5-amino-4-dichlorofluoromethanesulphenyl-1-(2,6-dichloro-4-trifluoromethyl-phenyl)pyrazole of melting point 100° C.-103° C. are obtained.

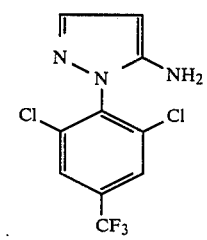

25 ml (27.6 g/0.3 mol) of 2-chloro-acrylonitrile are added dropwise to 24.5 g (0.1 mol) of 2,6-dichloro-4-trifluoromethylphenylhydrazine and with 20 mg of ethylenediamine-tetraacetic acid disodium salt (=Titriplex III) in 150 ml of methanol at the reflux temperature. After the addition is complete, the mixture is heated for a further 8 hours at the reflux temperature, 9 ml (0.16 mol) of 96% strength sulphuric acid are added dropwise, and the mixture is heated for a further 6 hours at the reflux temperature. 33.5 g (0.3 mol) of anhydrous sodium carbonate are added to the cooled reaction mixture. After 4 hours, the solvent is removed in vacuo, and the residue is taken up in 500 ml of water and stirred for 10 hours at room temperature. The deposit which precipitates is filtered off, rinsed with water and dried in vacuo at 50° C.

28.5 g (96% of theory) of 5-amino-1-(2,6-dichloro-4-trifluoromethylphenyl)-pyrazole of melting point 103° C.-105° C. are obtained.

EXAMPLE 2

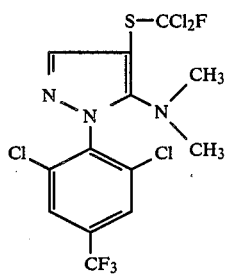

30 g (0.07 mol) of 5-amino-4-dichlorofluoromethanesulphenyl-1-(2,6-dichloro-4-trifluoromethylphenyl)-pyrazole are dissolved in 550 ml of dichloromethane, and 150 ml of 40 per cent strength aqueous sodium hydroxide solution, 3 spatula tips of tributylbenzylammonium chloride and 21 ml (0.22 mol) of 97 per cent purity dimethyl sulphate are added successively, and the mixture is stirred for 16 hours at room temperature. The aqueous phase is separated off, and the organic phase is washed with water and freed of solvent in vacuo. The residue is taken up in 300 ml of ethanol, 30 ml of 25 per cent strength aqueous ammonia are added, and the mixture is stirred for 5 to 10 hours. The solvent is then removed in vacuo, the residue is dissolved in 300 ml of dichloromethane, and the organic phase is washed successively with aqueous ammonium chloride solution and sodium chloride solution, dried over magnesium sulphate and concentrated in vacuo.

31.5 g (98.6% of theory) of 4-dichlorofluoromethanesulphenyl-5-dimethylamino-1-(2,6-dichloro-4-trifluoromethyl-phenyl)-pyrazole of melting point 85° C.-89° C. are obtained.

The following 1-aryl-pyrazoles of the general formula (I) are obtained in a corresponding fashion and according to the general instructions for the preparation:

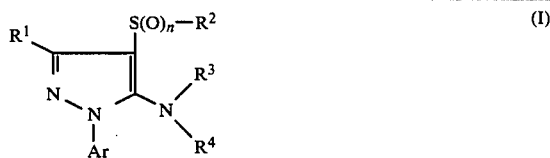

| Ex. No. | $R^1$ | $-S(O)_n-R^2$ | $-N\begin{matrix}R^3\\R^4\end{matrix}$ | Ar | Melting point °C. |
|---|---|---|---|---|---|
| 3 | H | —SO—CCl$_2$F | —N(CH$_3$)$_2$ | Cl—⟨⟩—CF$_3$ (2,6-diCl) | $^1$H—NMR(*): 2.83 |
| 4 | H | —SO$_2$—CCl$_2$F | —N(CH$_3$)$_2$ | Cl—⟨⟩—CF$_3$ (2,6-diCl) | $^1$H—NMR(*): 2.86 |
| 5 | H | —S—CClF$_2$ | —N(CH$_3$)$_2$ | Cl—⟨⟩—CF$_3$ (2,6-diCl) | M.p. 73° C.-74° C. |

-continued
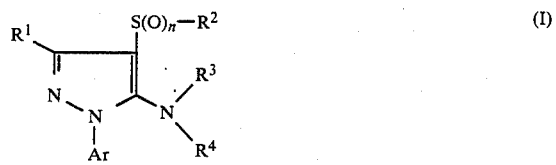
| Ex. No. | R¹ | —S(O)ₙ—R² | —N(R³)(R⁴) | Ar | Melting point °C. |
|---|---|---|---|---|---|
| 6 | H | —S—CF₃ | —N(CH₃)₂ | 2,6-Cl₂-4-CF₃-phenyl | M.p. 32° C.–36° C. |
| 7 | H | —SO₂—CCl₂F | —NH—(CH₂)₂—OCH₃ | 2,6-Cl₂-4-Br-phenyl | |
| 8 | —CH₃ | —SCF₃ | —N(CH₃)₂ | 2,6-Cl₂-4-CF₃-phenyl | Oil |
| 9 | —CH₃ | —SCF₃ | —N(CH₃)₂ | 2-Cl-4-CF₃-phenyl | Oil |
| 10 | —CH₃ | —SCCl₂F | —N(CH₃)₂ | 2,6-Cl₂-4-OCF₃-phenyl | Oil |
| 11 | —CH₃ | —SCClF₂ | —N(CH₃)₂ | 2,6-Cl₂-4-OCF₃-phenyl | Oil |
| 12 | —CH₃ | —SCF₃ | —N(CH₃)₂ | 2,6-Cl₂-4-OCF₃-phenyl | Oil |

-continued $$\text{(I)}$$

Structure: pyrazole with R¹ at 3-position, S(O)ₙ—R² at 4-position, NR³R⁴ at 5-position, Ar on N1.

| Ex. No. | R¹ | —S(O)ₙ—R² | —NR³R⁴ | Ar | Melting point °C. |
|---|---|---|---|---|---|
| 13 | —CH₃ | —SCCl₂F | —N(CH₃)₂ | 2-Cl-4-CF₃-phenyl | Oil |
| 14 | —CH₃ | —SCClF₂ | —N(CH₃)₂ | 2-Cl-4-CF₃-phenyl | Oil |
| 15 | —CH₃ | —SCCl₂F | —N(CH₃)₂ | 2,6-diCl-4-CF₃-phenyl | Oil |
| 16 | —CH₃ | —SCClF₂ | —N(CH₃)₂ | 2,6-diCl-4-CF₃-phenyl | Oil |
| 17 | H | —SCF₃ | —NH—CH₂—C₆H₅ | 2,6-diCl-4-CF₃-phenyl | 84 |
| 18 | H | —SCCl₂F | —NH—CH₂—C₆H₅ | 2,6-diCl-4-CF₃-phenyl | 97 |
| 19 | CH₃ | —S(O)CCl₂F | —N(CH₃)₂ | 2,6-diCl-4-CF₃-phenyl | 95–97 |
| 20 | CH₃ | —SO₂—CCl₂F | —N(CH₃)₂ | 2,6-diCl-4-CF₃-phenyl | 98–99 |

-continued $$(I)$$

Structure: pyrazole with R¹ at position 3, S(O)ₙ–R² at position 4, NR³R⁴ at position 5, and Ar on N1.

| Ex. No. | R¹ | –S(O)ₙ–R² | –N(R³)(R⁴) | Ar | Melting point °C. |
|---|---|---|---|---|---|
| 21 | CH₃ | –S(O)CF₃ | –N(CH₃)₂ | 2,6-dichloro-4-(CF₃)phenyl | 60–62 |
| 22 | H | –SCCl₂F | –N(C₂H₅)₂ | 2,6-dichloro-4-(CF₃)phenyl | $n_D^{20}$:** 1.5350 |
| 23 | H | –SCCl₂F | –N(CH₃)(C₂H₅) | 2,6-dichloro-4-(CF₃)phenyl | 65–71 |
| 24 | H | –SCF₃ | –N(C₂H₅)₂ | 2,6-dichloro-4-(CF₃)phenyl | $n_D^{20}$: 1.5057 |
| 25 | H | –SCF₃ | –N(CH₃)(C₂H₅) | 2,6-dichloro-4-(CF₃)phenyl | Oil |
| 26 | H | –SO₂CF₃ | morpholino | 2,6-dichloro-4-(CF₃)phenyl | 145–146 |
| 27 | H | –SO₂–CCl₂F | –N(CH₃)(C₂H₅) | 2,6-dichloro-4-(CF₃)phenyl | 92–95 |

(*)The ¹H NMR spectra were recorded in CDCl₃ with tetramethylsilane (TMS) as internal standard. The chemical shift is given as δ value in ppm.

USE EXAMPLES

In the following use examples, the compounds listed below were employed as comparison substances:

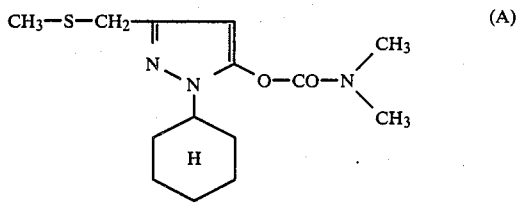

1-Cyclohexyl-5-[N,N-(dimethyl)-carbamoyloxy]-3-methylthiomethyl-pyrazole (known from DE-OS (German Published Specification) No. 2,839,270)

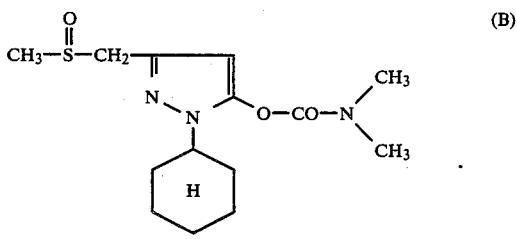

1-Cyclohexyl-5-[N,N-(dimethyl)-carbamoyloxy]-3-methylsulphinylmethyl-pyrazole (known from DE-OS (German Published Specification No. 2,839,270)

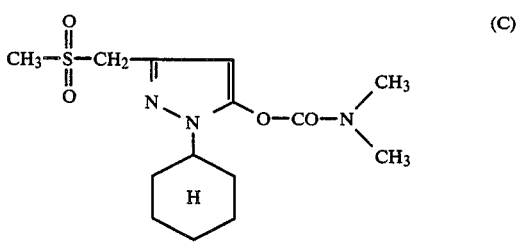

1-Cyclohexyl-5-[N,N-(dimethyl)-carbamoyloxy]-3-methylsulphonylmethyl-pyrazole (known from DE-OS (German Published Specification) No. 2,839,270).

EXAMPLE A

Phaedon larvae test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified periods of time, the destruction in % is determined. 100% means that all the beetle larvae have been killed; 0% means that none of the beetle larvae have been killed.

In this test, the following compounds of the preparation examples, for example, display superior action compared to the state of the art: (2), (5), (1) and (7).

EXAMPLE B

Plutella test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the cabbage moth (*Plutella maculipennis*), as long as the leaves are still moist.

After the specified periods of time, the destruction in % is determined. 100% means that all the caterpillars have been killed; 0% means that none of the caterpillars have been killed.

In this test, the following compounds of the preparation examples, for example, display superior action compared to the state of the art: (1), (2), (3), (4) (5) and (7).

EXAMPLE C

Tetranychus test (resistant)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, the following compounds of the preparation examples, for example, display superior action compared to the state of the art: (1), (3), (4) and (7).

EXAMPLE D

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the following compound of the preparation examples, for example, displays superior action compared to the state of the art: (2)

EXAMPLE E

Root-systemic action
Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all test insects have been killed and 0% if just as many test insects are still alive as in the case of the untreated control.

In this test, the following compound of the preparation examples, for example, displays superior action compared to the state of the art: (2).

EXAMPLE F

Root-systemic action
Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all test insects have been killed and 0% if just as many test insects are still alive as in the case of the untreated control.

In this test, the following compound of the preparation examples, for example, displays superior action compared to the state of the art: (2).

EXAMPLE G

Test insects: *Sitophilus granarius*
Solvent: Acetone 2 parts by weight of active compound are taken up in 1,000 parts by volume of solvent. The solution thus obtained is diluted with further solvent to the desired concentration.

2.5 ml of the active compound solution are pipetted into a Petri dish. A filter paper disc of about 9.5. cm diameter is located on the bottom of the Petri dish. The Petri dish is left standing open until the solvent has completely evaporated. The amount of active compound per $m^2$ of filter paper varies, depending on the concentration of the active compound solution. 25 test insects are then introduced into the Petri dish, and the dish is covered with a glass lid.

The condition of the test insects is checked 3 days after the experiments have been set up. The destruction in % is determined. 100% means that all the test insects have been killed; 0% means that none of the test insects have been killed.

In this test, the following compounds of the preparation examples, for examples, display superior action compared to the state of the art: (1), (2), (3), (5), (8), (13), (14), (9), (11), (12), (15) and (16).

EXAMPLE H

Test insects: *Blattella germanica*
Solvent: Acetone 2 parts by weight of active compound are taken up in 1,000 parts by volume of solvent. The solution thus obtained is diluted with further solvent to the desired concentration.

2.5 ml of the active compound solution are pipetted into a Petri dish. A filter paper disc of about 9.5 cm diameter is located on the bottom of the Petri dish. The Petri dish is left standing open until the solvent has completely evaporated. The amount of active compound per $m^2$ of filter paper varies, depending on the concentration of the active compound solution. 25 test insects are then introduced into the Petri dish, and the dish is covered with a glass lid.

The condition of the test insects is checked 3 days after the experiments have been set up. The destruction in % is determined. 100% means that all the test insects have been killed; 0% means that none of the test insects have been killed.

In this test, the following compounds of the preparation examples, for examples, display superior action compared to the state of the art: (2), (5), (8), (13), (14), (9), (11), (12) and (16).

EXAMPLE: I

Test with *Psoroptes ovis*
Solvent:
    35 parts by weight of ethylene glycol monomethyl ether 35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the desired concentration.

About 10–25 *Psoroptes ovis* are introduced into 1 ml of the active compound preparation to be tested, which has been pipetted into tablet nests of a deepdrawn pack. After 24 hours, the degree of destruction is determined.

In this test, the following compound of the preparation examples, for example, displays superior action compared to the state of the art: (1).

EXAMPLE K

Facefly test (*Musca autumnalis*)
Solvent:
  35 parts by weight of ethylene glycol monomethyl ether
  35 parts by weight of nonylphenol polyglycol ether To produce a suitable formulation, three parts by weight of active compound are diluted with seven parts of the abovementioned solvent/emulsifier mixture and the emulsion concentrate thus obtained is diluted with water to the particular desired concentration.

10 adult faceflies (*Musca autumnalis*) are introduced into Petri dishes containing filter paper discs of appropriate size which have been impregnated one day before the start of the test with 1 ml of the active compound preparation to be tested. After 3 hours, the degree of destruction is determined in per cent, 100% meaning that all of the flies have been destroyed and 0% meaning that no flies have been destroyed.

In this test, the following compound from the preparation examples, for example, displays superior action compared with the prior art: (2). EXAMPLE L
Test with parasitic, adult stable flies (*Stomoxys calcitrans*)
Solvent: Cremophor To produce a suitable preparation of active compound, three parts by weight of active compound are mixed with seven parts by weight of the solvent mixture indicated above, and the concentrate thus obtained is diluted with water to the particular desired concentration.

10 adult stable flies *Stomoxys* calcitrans are placed in Petri dishes containing sandwiches of appropriate size which have been saturated one day before the start of the experiment with 1 ml of the active compound preparation to be tested. After 3 hours, the degree of destruction is determined, 100% denoting that all the flies have been killed and 0% denoting that none have been killed.

In this test, the following compound of the preparation examples, for example, displays superior action compared to the state of the art: (2).

EXAMPLE M

Test insect: *Diabrotica balteata* Larvae (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l) being decisive.

The soil is filled into pots having a volume of 0.5 l and the pots are left to stand at 20° C.

Immediately after the filling of the pot, 6 pre-germinated corn grains are introduced into each pot. After two days the respective test animals are introduced into the treated soil. After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compounds from the preparation examples show a superior action compared to the prior art: (3), (5), (12), (16).

It is understood that the specification and examples are illustrative but not limitative of the present invention and that other embodiments within the spirit and scope of the invention will suggest themselves to those skilled in the art.

We claim:

1. A 1-aryl-pyrazole of the formula

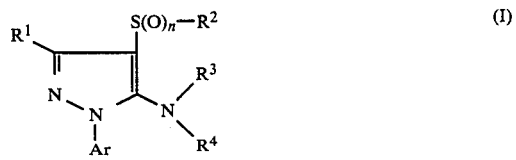

in which
R$^1$ represents hydrogen, or alkyl or halogenoalkyl having 1 to 4 carbon atoms,
R$^2$ represents straight-chain or branched halogenoalkyl having up to 8 carbon atoms and up to 17 identical or different halogen atoms,

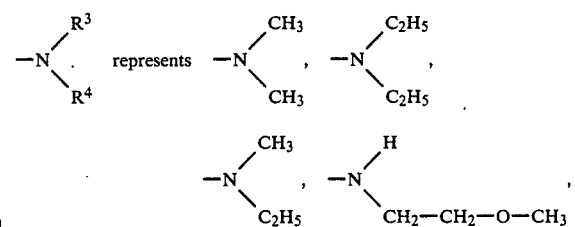

pyrrolidinyl, piperidinyl, perhydroazepinyl or morpholinyl,
Ar represents phenyl mono- or poly-substituted by identical or different residues selected from CN, NO$_2$, halogen C$_1$–C$_4$-alkyl, C$_1$–C$_4$-alkoxy, C$_1$–C$_4$-alkoxycarbonyl, halogeno-C$_1$–C$_4$-alkyl, halogeno-C$_1$–C$_4$-alkoxy, and
n represents 0, 1 or 2.

2. A 1-aryl-pyrazole according to claim 1, in which
R$^1$ represents hydrogen, methyl, ethyl, n- or ipropyl or trifluoromethyl,
R$^2$ represents chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptapfluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorodibromomethyl, difluorobromomethyl, or fluorochlorobromomethyl, $R^3$ and $R^4$, together with the nitrogen atom to which they are bound, represent pyrrolidinyl, piperidinyl, perhydroazepinyl or moropholinyl, and Ar represents optionally mono- to pentasubstituted phenyl, the substituents being identical or different and being selected rom the group consisting of cyano, nitro, fluorine, chlorine, bromine, iodine, methyl, ethyl, n- and i-propyl, n-, i-, s- and t-bytyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethyoxy, pentafluoroethoxy, tetrafluoroethoxy, trifluorochlroethoxy, trifluoroethoxy, difluorodichloroethoxy, trifluorodichloroethoxy, or pentachloroethoxy.

3. A compound according to claim 1, wherein such compound is 4-dichlorofluoromethane-sulphonyl-5-(2-methoxyethyl)-amino-1-(2,6-dichloro-4-trifluoromethyl-phenyl)-pyrazole of the formula

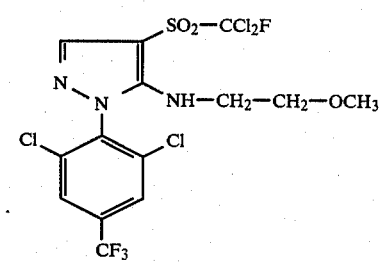

4. A compound according to claim 1, wherein such compound is 4-dichlorofluoromethanesulphenyl-5-dimethylamino-1-(2,6-dichloro-4-trifluoromethyl-phenyl)-pyrazole of the formula

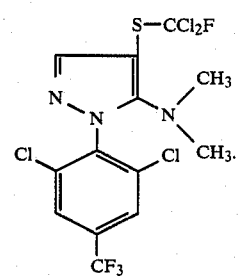

5. A compound according to claim 1 wherein such compound is 4-dichlorofluoromethanesulphonyl-5-dimethylamino-1-(2,6-dichloro-4-trifluoromethyl-phenyl)-pyrazole of the formula

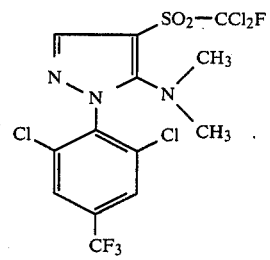

6. A compound according to claim 1 wherein such compound is 5-dimethylamino-3-methyl-4-trifluoromethylthio-1-(2,6-dichloro-4-trifluoromethoxy-phenyl)-pyrazole of the formula

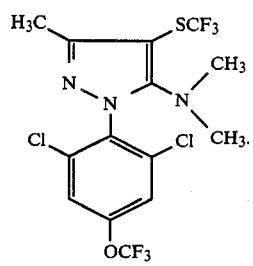

7. A compound according to claim 1 wherein such compound is 4-chlorodifluoromethylthio-5-dimethylamino-3-methyl-1-(2,6-dichloro-4-trifluoromethyl-phenyl)-pyrazole of the formula

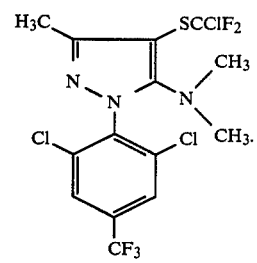

8. A compound according to claim 1 wherein such compound is 4-dichlorofluoromethylthio-5-diethylamino-1-(2,6-dichloro 4-trifluoromethyl-phenyl)-pyrazole of the formula

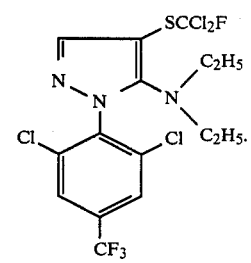

9. A compund according to claim 1 wherein such compound is 4-dichlorofluoromethylthio-5-(N-methyl-N-ethyl-amino)-1-(2,6-dichloro-4-trifluoromethyl-phenyl)-pyrazole of the formula

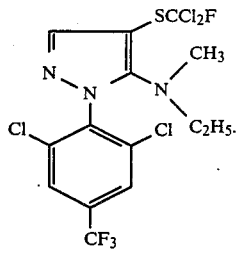

10. An insecticidal or acaricidal composition comprising an insecticidally or acaricidally effective amount of a compound according to claim 1 in admixture with a diluent.

11. A method of combating insects or acarids which comprises applying to such insects or acarids or to a habitat thereof an insecticidally or acarididally effective amount of a compound according to claim 1 in admixture with a diluent.

12. The method according to claim 11, wherein such compound 4-dichlorofluoromethane-sulphonyl-5-(2-methoxyethyl)-amino-1-(2,6-dichloro-4-trifluoromethyl-phenyl)-pyrazole, 4-dichlorofluoromethanesulphenyl-5-dimethylamino-1-(2,6-dichloro-4-trifluoromethyl-phenyl)-pyrazole, 4-dichlorofluoromethanesulphonyl-5-dimethylamino-1-(2,6-dichloro-4-trifluoromethyl-phenyl)-pyrazole, 5-dimethylamino-3-methyl-4-trifluoromethylthio-1(2,6-dichloro-4-trifluoromethoxy-phenyl)-pyrazole, 4-chlorodifluoromethylthio-5-dimethylamino-3-methyl-1-(2,6-dichloro-4-trifluoromethyl-phenyl)-pyrazole, 4-dichlorofluoromethylthio-5-diethylamino-1-(2,6-dichloro-4-trifluoromethyl-phenyl)-pyrazole or 4-dichlorofluoromethylthio-5-(N-methyl-N-ethyl-amino)-1-(2,6-dichloro-4-trifluoromethyl-phenyl)-pyrazole.

* * * * *

UNITED STATES PATENT AND TRADEMARK OFFICE
CERTIFICATE OF CORRECTION

PATENT NO. : 4,771,066

DATED : September 13, 1988

INVENTOR(S) : Reinhold Gehring, et al

It is certified that error appears in the above-identified patent and that said Letters Patent is hereby corrected as shown below:

| | |
|---|---|
| Col. 2, lines 45-46 | After "acceptor," insert --or when-- |
| Col. 5, line 62 | Delete "monoto" and substitute --mono- to-- |
| Col. 15, line 5 | Delete "-HBr" and substitute -- -HCl -- |
| Col. 18, line 4 | After "$R^5$-" delete "D" and substitute --$O^1$-- |
| Col. 18, line 40 | Delete "$Hal_1$" and substitute --$Hal^1$-- |
| Col. 18, line 45 | After "$H_2N$-" delete "$4^{4-1}$" and substitute --$R^{4-1}$-- |
| Col. 23, line 29 | Delete "twophase" and substitute --two-phase-- |
| Col. 25, line 26 | Delete "The" and substitute --the-- |
| Col. 27, line 28 | Delete "surfaceactive" and substitute --surface-active-- |
| Col. 28, lines 36-37 | Delete "conceptration" and substitute --concentration-- |
| Col. 30, line 40 | After "mol" delete " ) " and substitute --)-- |
| Col. 31, after formula of Example 2 | Insert --(Process b)-- |
| Col. 44, line 57 | After "-alkyl," insert --or-- |
| Col. 44, line 61 | Delete "ipropyl" and substitute --i-propyl-- |
| Col. 45, line 12 | Delete "rom" and substitute --from-- |
| Col. 45, line 15 | Delete "bytyl" and substitute --butyl-- |

UNITED STATES PATENT AND TRADEMARK OFFICE
CERTIFICATE OF CORRECTION

PATENT NO. : 4,771,066

DATED : September 13, 1988

INVENTOR(S) : Reinhold Gehring, et al

It is certified that error appears in the above-identified patent and that said Letters Patent is hereby corrected as shown below:

Col. 46, line 50      After "dichloro" isert -- - --
Col. 46, line 65      Correct spelling of --compound--
Col. 48, line 4       After "compound" insert --is--

Signed and Sealed this

Thirtieth Day of May, 1989

Attest:

DONALD J. QUIGG

Attesting Officer      Commissioner of Patents and Trademarks